US006362378B1

(12) United States Patent
Jacquot et al.

(10) Patent No.: US 6,362,378 B1
(45) Date of Patent: Mar. 26, 2002

(54) METHOD FOR ETHERIFYING A BENZYL ALCOHOL, RESULTING PRODUCTS AND APPLICATIONS

(75) Inventors: Roland Jacquot, Francheville; Michel Spagnol, Meyzieu, both of (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/462,432

(22) PCT Filed: Jul. 8, 1998

(86) PCT No.: PCT/FR98/01472

§ 371 Date: Mar. 14, 2000

§ 102(e) Date: Mar. 14, 2000

(87) PCT Pub. No.: WO99/02475

PCT Pub. Date: Jan. 21, 1999

(30) Foreign Application Priority Data

Jul. 9, 1997 (FR) .............................. 97/08733

(51) Int. Cl.[7] .............................................. C07C 41/09
(52) U.S. Cl. .................. 568/644; 568/652; 424/65; 424/69; 424/70.1; 424/400; 424/401; 512/1; 512/8; 512/9; 512/19; 512/20; 512/23
(58) Field of Search ................. 568/644, 652; 424/65, 69, 70.1, 400, 401; 512/1, 8, 9, 19, 20, 23

(56) References Cited

U.S. PATENT DOCUMENTS 4,147,671 A    4/1979  Boelens ...................... 252/522
4,657,700 A  * 4/1987  Ochsner ................. 252/522 R

FOREIGN PATENT DOCUMENTS

| CH | 681 778 A5 | 5/1993 | ............ A61K/7/46 |
| DE | 154658 | 8/1903 | |
| DE | 35 02 188 A | 7/1986 | ............ C07C/43/18 |
| DE | 44 34 823 | 4/1996 | ......... C07C/43/178 |
| EP | 0 137 419 | 4/1985 | ............ A61K/7/46 |
| EP | 0 258 172 | 3/1988 | ............. C11B/9/00 |
| WO | WO 95/00467 | 1/1995 | ............ C07C/41/09 |

OTHER PUBLICATIONS

XP-002081064—"Perfume and Flavor Chemicals" No Month Provided 1969, Arctander, Montclair, NJ See Nos. 311, 312, 313, 336, 337, 1919.
XP-002081410—H. Bohnsack: "Beitrag Zur Kenntnis der ätherischen Oele . . . " Reichstoffe Aromen Korperpflegemittel, vol. 15, No. 11, Nov. 1965, pp. 407–410.
XP-002056679—M.J. Climent: "Hydride transfer reactions of benzylic alcohols catalyzed by acid faujasites" Recueil Des Travaux Chimiques Des Pays–Bas, vol. 110, No. 6, Jun. 1991, pp. 275–278.
XP-002056680—T. M. Wortel: "Zeolite catalyzed liquid phase dehydration of alpha–penylethanols" Acta Phys. Chem., vol. 24, No. 1–2, No Month Provided 1978, pp. 341–346.
International Search Report.

* cited by examiner

Primary Examiner—Rosalynd Keys

(57) ABSTRACT

The present invention relates to a process for etherification of a benzyl type alcohol, to the products obtained and to their applications, in particular in the perfumery field. The etherification process of the invention consists of reacting a benzyl type alcohol with another alcohol in the presence of a catalyst, characterized in that the etherification reaction is carried out in the presence of an effective quantity of a zeolite.

37 Claims, No Drawings

METHOD FOR ETHERIFYING A BENZYL ALCOHOL, RESULTING PRODUCTS AND APPLICATIONS

This application is an application under 35 U.S.C. Section 371 of International Application Number PCT/FR98/01472, filed on Jul. 8, 1998.

The present invention relates to a process for etherification of a benzyl tpe alcohol, to the products obtained and to their applications, in particular in the perfumery field.

German patent DE-4 434 823 shows that it is known to prepare hydroxybenzyl alcohol ethers by reacting the hydroxybenzyl alcohol and an alkanol in the presence of a sulphonic resin (Amberlyst®) A21). The resin is hard to regenerate and the reaction yield obtained is not very satisfactory as it is only 72%.

That process is not compatible with an industrial application.

The precise aim of the present invention is to propose a process which can overcome these disadvantages.

We have now discovered a process for etherifing a benzyl type alcohol consisting of reacting said alcohol with another alcohol in the presence of a catalyst, said process being characterized in that the etherification reaction is carried out in the presence of an effective quantity of a zeolite. This constitutes the subject matter of the present invention.

In the following description of the present invention, the term "by a benzyl type alcohol" means an aromatic heterocycle or carbocycle wherein one hydrogen atom directly bonded to the aromatic ring is replaced by a group:

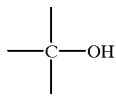

and the term "aromatic" means the conventional concept of aromaticity as defined in the literature, in particular by Jerry MARCH, Advanced Organic Chemistry, 4$^{th}$ edition, John Wiley & Sons, 1992, pp. 40 ff.

For simplicity, the other alcohol used will be designated by the generic term "alkanol" which also encompasses alcohols containing cycles, in particular aromatics.

More precisely, the present invention provides a process for etherification of a benzyl alcohol with general formula (I):

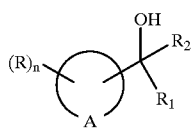

where:
A represents the residue of a cycle forming all or a portion of a carbocyclic or heterocyclic aromatic, monocyclic or polycyclic system comprising at least one group:

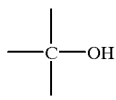

R represents one or more substituents which may be identical or different;

$R_1$ and $R_2$, which may be identical or different, represent a hydrogen atom, a functional group or a hydrocarbon group containing 1 to 24 carbon atoms, which can be a saturated or unsaturated, linear or branched acyclic aliphatic group; a saturated, unsaturated or aromatic, monocyclic or polycyclic cycloaliphatic group; or a saturated or unsaturated, linear or branched aliphatic group carrying a cyclic substituent;

$R_1$ and $R_2$ can form a cycle optionally comprising a further heteroatom;

n is a number equal to 5 or less.

The benzyl type alcohol used in the process of the invention has formula (I) where $R_1$ or $R_2$ represent a saturated or unsaturated, linear or branched acyclic aliphatic group.

More preferably, $R_1$ and $R_2$ represent a linear or branched alkyl group containing 1 to 12 carbon atoms, preferably 1 to 6 carbon atoms: the hydrocarbon chain can optionally be interrupted by a heteroatom (for example oxygen), by a functional group (for example —CO—) and/or may carry a substituent (for example a halogen).

The saturated or unsaturated, linear or branched acyclic aliphatic group can optionally carry a cyclic substituent. The term "cycle" preferably means a saturated, unsaturated or aromatic carbocyclic or heterocyclic cycle, preferably cycloaliphatic or aromatic, in particular cycloaliphatic comprising 6 carbon atoms in the cycle, or benzenic.

The acyclic aliphatic group can be connected to the cycle by a valence bond, a heteroatom or a functional group and examples are given below.

The cycle can optionally be substituted and examples of cyclic substituents include, inter alia, substituents such that R has the meaning given above.

$R_1$ and $R_2$ can also represent a carbocyclic group which is saturated or contains 1 or 2 unsaturated bonds in the cycle, generally containing 3 to 8 carbon atoms, preferably 6 carbon atoms in the cycle; said cycle can be substituted by substituents such as R.

$R_1$ and $R_2$ can also represent an aromatic carbocyclic group, preferably monocyclic, generally containing at least 4 carbon atoms, preferably 6 carbon atoms per cycle; said cycle can be substituted by substituents such as R.

One of groups $R_1$ and $R_2$ can represent a group $CF_3$.

In formula (I), groups $R_1$ and $R_2$ can form a cycle between them, preferably containing 5 to 7 atoms, saturated or unsaturated, optionally containing a further heteroatom, for example an oxygen atom.

The invention is also applicable to benzyl type alcohols with formula (I) in which A is the residue of a cyclic compound preferably containing at least 4 atoms in the cycle, preferably 5 or 6, optionally substituted, and representing at least one of the following cycles:

an aromatic, monocyclic or polycyclic carbocycle;
an aromatic, monocyclic or polycyclic heterocycle containing at least one of the heteroatoms O, N and S.

Without in any way limiting the scope of the invention, optionally substituted residue A represents a residue:
of a monocyclic carbocyclic, aromatic compound such as benzene or toluene;
of a polycyclic condensed aromatic compound such as naphthalene;
of a monocyclic heterocyclic, aromatic compound such as pyridine, furane, or thiophene.

In the process of the invention, an aromatic compound with formula (I) is preferably used in which A represents a benzene or a naphthene ring.

The residue A of the benzyl type alcohol with formula (I) can carry one or more substituents.

The number of substituents present on the cycle depends on the carbon condensation of the cycle and on the presence or otherwise of unsaturated bonds on the cycle.

The maximum number of substituents which can be carried by the cycle can readily be determined by the skilled person.

In the present text, the term "several" generally means less than 5 substituents on an aromatic ring.

Examples of substituents are given below but this list is not limiting in nature. The following can in particular be cited:

linear or branched alkyl groups preferably containing 1 to 6 carbon atoms, more preferably 1 to 4 carbon atoms;

linear or branched alkenyl groups, preferably containing 2 to 6 carbon atoms, more preferably 2 to 4 carbon atoms;

linear or branched halogenoalkyl groups preferably containing 1 to 6 carbon atoms, more preferably 1 to 4 carbon atoms;

cycloalkyl groups containing 3 to 6 carbon atoms, preferably the cyclohexyl group;

the phenyl group;

the hydroxyl group;

the $NO_2$ group;

alkoxy $R_3$—O— or thioether $R_3$—S— groups where $R_3$ represents a linear or branched alkyl group containing 1 to 6 carbon atoms, more preferably 1 to 4 carbon atoms, or the phenyl group;

—N—$(R_4)_2$ groups where groups $R_4$, which may be identical or different, represent a hydrogen atom, a linear or branched alkyl group containing 1 to 6 carbon atoms, more preferably 1 to 4 carbon atoms, or a phenyl group;

—NH—CO—$R_4$ groups, where group $R_4$ has the meaning given above;

carboxy groups or $R_4$—O—CO— derivatives where group $R_4$ has the meaning given above;

acyloxy or aroyloxy groups $R_3$—CO—O— where group $R_3$ has the meaning given above;

a halogen atom, preferably a fluorine atom;

a $CF_3$ group.

When n is 2 or more, two groups R and the 2 successive atoms of the aromatic cycle can be connected together by an alkylene, alkenylene or alkenylidene group containing 2 to 4 carbon atoms to form a saturated, unsaturated or aromatic heterocycle containing 5 to 7 carbon atoms. One or more carbon atoms can be replaced by a further heteroatom, preferably oxygen. Thus the groups R can represent a methylenedioxy or ethylenedioxy group.

The preferred substituents are selected from electron-donating groups.

The term "electron-donating group" means a group as defined by H. C. BROWN in the work by Jerry MARCH—Advanced Organic Chemistry, chapter 9, pages 243 and 244 (1985).

The process of the invention is of particular application to benzyl type alcohols with formula (Ia):

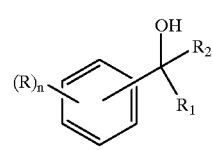

(Ia)

where:

n is a number equal to 4 or less, preferably 0, 1 or 2;

group R is an electron-donating group, preferably an alkyl, alkoxy, methylenedioxy or ethylenedioxy group;

groups $R_1$ and $R_2$, which may be identical or different, represent:
  a hydrogen atom;
  a linear or branched alkyl group containing 1 to 6 carbon atoms, preferably 1 to 4 carbon atoms, such as methyl, ethyl, propyl, isopropyl, butyl, isobutyl, sec-butyl or tert-butyl;
  a cycloalkyl group containing 3 to 8 carbon atoms, preferably a cyclopentyl or cyclohexyl group;
  a phenyl group;
  a phenylalkyl group containing 7 to 12 carbon atoms, preferably a benzyl group;
  a $CF_3$ group.

Preferred compounds with formula (Ia) are those in which:

n is a number equal to 0, 1 or 2;

groups R, which may be identical or different, represent an alkyl, alkoxy, methylenedioxy or ethylenedioxy group, or a hydroxyl group;

groups $R_1$ and $R_2$, which may be identical or different, re:
  a hydrogen atom;
  a linear or branched alkyl group containing 1 to 6 carbon atoms, preferably 1 to 4 carbon atoms, such as methyl, ethyl, propyl, isopropyl, butyl, isobutyl, sec-butyl or tert-butyl.

The benzyl type alcohols which are preferably used in the process of the invention are:

vanillic alcohol;

p-hydroxybenzyl alcohol;

1-(4-hydroxy-3-methoxyphenyl)ethanol;

2-hydroxybenzyl alcohol;

p-methoxybenzyl alcohol;

3,4-dimethoxybenzyl alcohol;

6-n-propyl-3,4-dimethoxybenzyl alcohol;

(3,4-dimethoxyphenyl)dimethylcarbinol;

1-[1-hydroxy-2-methylpropyl]-3,4-dimethoxybenzene;

1-[1-hydroxy-2-methylpropyl]-3,4-diethoxybenzene;

1-[1-hydroxyethyl]-3,4-diethoxybenzene;

1-[1-hydroxyethyl]-3,4-dimethoxy-6-propylbenzene;

5-[1-hydroxyethyl]-1,3-benzodioxol;

naphthalene-2-methylol.

More particularly, the alkanol has the following general formula (II):

$$R_5\text{—OH} \quad (II)$$

in which formula (II):

$R_5$ represents a hydrocarbon group containing 1 to 24 carbon atoms, which can be a saturated or unsaturated, linear or branched acyclic aliphatic group; a saturated, unsaturated or aromatic cycloaliphatic group; or a saturated or unsaturated, linear or branched aliphatic group carrying a cyclic substituent.

The alkanol used in the process of the invention has formula (II) where $R_5$ represents a saturated or unsaturated, linear or branched acyclic aliphatic group.

More precisely, $R_5$ represents a linear or branched alkyl, alkenyl, alkadienyl or alkynyl group preferably containing 1 to 24 carbon atoms.

The hydrocarbon chain can optionally be:

interrupted by one of the following groups:

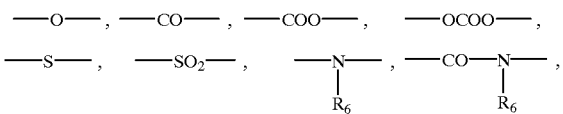

where $R_6$ represents hydrogen or a linear or branched alkyl group containing 1 to 4 carbon atoms, preferably a methyl or ethyl group;

and/or a carrier of one of the following groups:

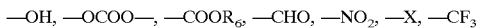

where $R_6$ has the meaning given above.

The saturated or unsaturated, linear or branched acyclic aliphatic residue can optionally carry a cyclic substituent. The term "cycle" means a saturated, unsaturated or aromatic carbocyclic or heterocyclic cycle.

The acyclic aliphatic residue can be connected to the cycle by a valence bond or by one of the following groups:

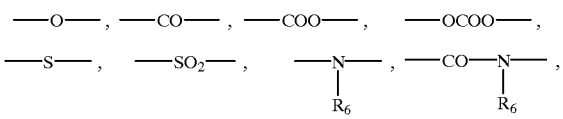

where $R_6$ has the meaning given above.

Examples of cyclic substituents are cycloaliphatic, aromatic or heterocyclic substituents, in particular cycloaliphatic substituents containing 6 carbon atoms in the cycle, or benzenic, these cyclic substituents themselves optionally carrying 1, 2, 3, 4 or 5 groups R', which may be identical or different, R' having the meaning given above for group R carried by the cycle with formula (I).

In the general alkanol formula (II), $R_5$ can also represent a carbocyclic group which is saturated or contains 1 or 2 unsaturated bonds in the cycle, generally containing 3 to 7 carbon atoms, preferably 6 carbon atoms in the cycle; said cycle can be substituted by 1 to 5 R' groups, preferably 1 to 3; R' has the same meanings defined above for R.

Preferred examples of groups $R_5$ which can be cited are cyclohexyl and cyclohexene-yl groups, optionally substituted with linear or branched alkyl groups containing 1 to 4 carbon atoms.

The process is readily carried out using the majority of alkanols. Examples of alkanols are:

lower aliphatic alkanols containing 1 to 5 carbon atoms, such as methanol, ethanol, trifluoroethanol, propanol, isopropyl alcohol, butanol, isobutyl alcohol, sec-butyl alcohol, tert-butyl alcohol, pentanol, isopentyl alcohol, sec-pentyl alcohol and tert-pentyl alcohol, ethylene glycol monoethyl ether, methyl lactate, isobutyl lactate, methyl D-lactate, isobutyl D-lactate, 3-chlorobut-2-ene-1-ol, and 2-butyn-1-ol;

higher aliphatic alcohols containing at least 6 and up to about 20 carbon atoms, such as hexanol, heptanol, isoheptyl alcohol, octanol, isooctyl alcohol, 2-ethylhexanol, sec-octyl alcohol; tert-octyl alcohol, nonanol, isononyl alcohol, decanol, dodecanol, tetradecanol, octadecanol, hexadecanol, oleyl alcohol, eicosyl alcohol, or diethyleneglycol monoethyl ether;

cycloaliphatic alcohols containing 3 to about 20 carbon atoms, such as cyclopropanol, cyclobutanol, cyclopentanol, cyclohexanol, cycloheptanol, cyclooctanol, cyclododecanol, tripropylcyclohexanol, methylcyclohexanol and methylcycloheptanol, cyclopenten-ol or cyclohexen-ol;

an aliphatic alcohol carrying an aromatic group containing 7 to about 20 carbon atoms, such as benzyl alcohol, phenethyl alcohol, phenylpropyl alcohol, phenyloctadecyl alcohol and naphthyldecyl alcohol.

It is also possible to use polyols, in particular polyoxyethyleneglycols such as ethylene glycol, diethylene glycol, triethylene glycol, propylene glycol or glycerol.

Of the alcohols cited above, aliphatic or cycloaliphatic alcohols, preferably primary or secondary aliphatic alcohols containing 1 to 4 carbon atoms and cyclohexanol, are preferably used in the process of the invention.

In a preferred variation of the process of the invention, a terpene alcohol is used, more particularly a terpene alcohol with formula (IIa):

$$T-OH \qquad (IIa)$$

in which formula (IIa):

T represents a terpene alcohol residue containing multiples of 5 carbon atoms.

The term "terpene" as used in the remainder of the description means oligomers derived from isoprene.

More precisely, the alcohol used has general formula (IIa) where residue T represents a hydrocarbon group containing 5 to 40 carbon atoms, more particularly a saturated or unsaturated, linear or branched aliphatic group; a saturated, unsaturated or aromatic, monocyclic or polycyclic cycloaliphatic group, comprising cycles containing 3 to 8 carbon atoms.

More precisely and without in any way limiting the scope of the invention, residue T represents:

a saturated or unsaturated, linear or branched aliphatic terpene alcohol;

a saturated or unsaturated monocyclic cycloaliphatic or aromatic terpene alcohol;

a cycloaliphatic or polycyclic terpene alcohol containing at least two saturated and/or unsaturated carbocycles.

If residue T is a saturated or unsaturated, linear or branched aliphatic terpene alcohol, the number of carbon atoms is between 5 and 40 carbon atoms. More specific examples of residue T which can be mentioned are groups containing 8 carbon atoms, saturated or with a double bond, and carrying two methyl groups, preferably in the 3 and 7 position.

When the compound is a monocyclic compound, the number of carbon atoms in the cycle can vary widely, between 3 and 8 carbon atoms, but preferably 5 or 6 carbon atoms, and is usually carried by an aliphatic chain.

The carbocycle can be saturated or comprise 1 or 2 unsaturated bonds in the cycle, preferably 1 to 2 double bonds which are usually in the position α to the oxygen atom.

With an aromatic terpene alcohol, the aromatic cycle is generally a benzene ring.

The compound can also be polycyclic, preferably bicyclic meaning that at least two cycles have two carbon atoms in common. In the case of polycyclic compounds, the number of carbon atoms in each cycle is in the range 3 to 6; the total number of carbon atoms is preferably equal to 7.

Examples of the bicyclic structure which are currently encountered are:

[4,1,0]

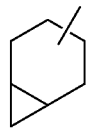

[2,2,1]

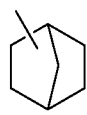

[3,1,1]

[3,2,0]

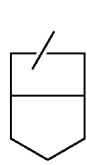

For a cycle, the presence of substituents is not excluded provided that they are compatible with the envisaged application. The substituents usually carried by the carbocycle are one or more alkyl groups, preferably three methyl groups, a methylene group (corresponding to an exocyclic bond) or an alkenyl group, preferably an isopropenyl group.

Examples of terpene alcohols which can be used are:
saturated or unsaturated aliphatic terpene alcohols such as:
  3,7-dimethyloctanol;
  tetrahydro-allocimenol;
  hydroxycitronellol;
  1-hydroxy-3,7-dimethyl-7-octene;
  nerol;
  geraniol;
  linalool;
  citronellol;
  3,7 dimethyloct-6-en-1-ol;
  1-hydroxy-2-ethyl-5-isopropyl-8-methyl-2,7-nonadiene;
  1-hydroxy-3,7,11-trimethyl-6,10-dodecadiene;
aromatic cycloaliphatic terpene alcohols such as:
  thymol;
saturated or unsaturated monocyclic or polycyclic cycloaliphatic terpene alcohols such as:
  chrysanthemic alcohol;
  1-hydroxyethyl-2,2,3-trimethylcyclopentane;
  terpinol hydrate;
  1,8-terpin;
  dihydro-terpineol;
  β-terpineol;
  perillylic alcohol;
  1-methyl-3-hydroxy-4-isopropylcyclohexene;
  α-terpineol
  terpinene-4-ol;
  1,3,5-trimethyl-4-hydroxymethylcyclohexene;
  carveol;
  cis-2-pinanol;
  cis-3-pinanol;
  isoborneol;
  verbenol;
  trans-pinocarveol;
  campholenic alcohol;
  5-(2,3-dimethyl-tricyclo-[2.2.1.0$^{2.6}$]-hept-3-yl)-2-methyl-2-penten-1-ol, or santanol.

Of the above alcohols, the following alcohols are preferred:
  chrysanthemic alcohol;
  3,7-dimethyloctanol;
  geraniol;
  linalool;
  citronellol;
  hydroxycitronellol;
  nerol;
  thymol;
  menthol;
  isoborneol;
  verbenol.

In accordance with the process of the invention, the hydroxyalkylation reaction is carried out in the presence of a catalyst constituted by a zeolite.

The term "zeolite" means a crystallised tectosilicate of natural or synthetic origin the crystals of which are produced by a three-dimensional assembly of tetrahedral $SiO_4$ and $TO_4$ units: T represents a trivalent element such as aluminium, gallium, boron or iron, preferably aluminium.

Aluminosilicate type zeolites are the most common.

Inside the crystalline framework, zeolites have a system of cavities connected to each other by channels with a well defined diameter which are known as pores.

The zeolites can have a unidimensional, two-dimensional or three-dimensional network.

A natural or synthetic zeolite is used in the process of the invention.

Examples of natural zeolites which can be used are: chabazite, cliniptilolite, erionite, phillipsite and offretite.

Synthetic zeolites are well suited for implementing the invention.

Examples of synthetic zeolites with a unidimensional network are ZSM-4 zeolite, L zeolite, ZSM-12 zeolite, ZSM-22 zeolite, ZSM-23 zeolite and ZSM-48 zeolite.

Examples of two-dimensional network zeolites which are preferably used are mordenite and ferrierite.

More particular examples of zeolites with a three dimensional network are β zeolite, Y zeolite, X zeolite, ZSM-5 zeolite, ZSM-11 zeolite and offretite.

Synthetic zeolites are preferably used, more particularly zeolites in the following forms:
  mazzite with an Si/Al mole ratio of 3.4;
  L zeolite with an Si/Al mole ratio of 1.5 to 3.5;
  mordenite with an Si/Al mole ratio of 5 to 150, preferably 10 to 100 and more, preferably 10 to 25;
  ferrierite with an Si/Al mole ratio of 3 to 10;
  offretite with an Si/Al mole ratio of 4 to 8.5;
  β zeolites with an Si/Al mole ratio of more than 8, preferably in the range 10 to 100, more preferably in the range 12 to 50;
  Y zeolites, in particular zeolites obtained after a dealumination treatment (for example hydrotreatment, washing with hydrochloric acid or treatment with SiCl$_4$) more particularly US-Y zeolites with an Si/Al mole ratio of more than 3, preferably in the range 6 to 60;

Faujasite type X zeolite with an Si/Al mole ratio of 0.7 to 1.5;

ZSM-5 zeolites or aluminium silicalite with an Si/Al mole ratio of 10 to 500;

ZSM-11 zeolite with an Si/Al mole ratio of 5 to 30;

MCM type mesoporous zeolite, more particularly MCM-22 and MCM-41 with an Si/Al mole ratio in the range 10 to 100, preferably in the range 15 to 40.

Of all these zeolites, β zeolites are preferably used in the process of the invention.

The zeolites used in the process of the invention are known products which have been described in the literature (see "Atlas of Zeolites, Structure Types" by W. M. Meier and D. H. Olson published by the Structure Commission of the International Zeolite Association (1992)].

Commercially available zeolites are used, or they are synthesised using the processes described in the literature.

Reference may be made to the Atlas described above, and more particularly, for the preparation of:

L zeolite, to the publication by Barrer R. M. et al., Z. Kristallogr., 128, pp. 352 (1969);

ZSM-12 zeolite, to U.S. Pat. No. 3,832,449 and the article by LaPierre et al., Zeolites 5 pp. 346 (1985);

ZSM-22 zeolite, to the publication by Kokotailo G. T. et al., Zeolites 5, pp. 349 (1985);

ZSM-23 zeolite, to U.S. Pat. No. 4,076,842 and to the article by Rohrman A. C. et al., Zeolites 5, pp. 352 (1985);

ZSM-48 zeolite, to the work by Schenker, J. L. et al., Zeolites 5, pp. 355 (1985);

β zeolite, to U.S. Pat. No. 3,308,069 and to the article by Caullet P. et al., Zeolites 12, pp. 240 (1992);

mordenite, to the work by Itabashi et al., Zeolites 6, pp. 30 (1986);

X and Y zeolites, to U.S. Pat. Nos. 2,882,244 and 3,130,007 respectively;

ZSM-5 zeolite, to U.S. Pat. No. 3,702,886 and to the article by Shiralkar V. P. et al., Zeolites 9, pp. 363 (1989);

ZSM-11 zeolite, to the work by Harrison I. D. et al., Zeolites 7, pp. 21(1987);

solid mesoporous MCM or zeolite, to the article by Beck et al., J. Am. Chem. Soc., 114 (27), pp. 10834–43 (1992).

In order to use a zeolite with the desired Si/Al atomic ratio, it may be necessary to carry out a dealumination treatment.

Methods which are known to the skilled person can be used, non exhaustive examples of which include calcining in the presence of a vapour, calcining in the presence of steam followed by attack with mineral acids (HNO$_3$, HCl . . . ), direct dealumination treatments with reactants such as silicon tetrachloride (SiCl$_4$), ammonium hexafluorosilicate ((NH$_4$)$_2$SiF$_6$), or ethylenediaminetetracetic acid (EDTA) and its mono- or disodium form. It is also possible to carry out a dealumination treatment by direct acid attack using solutions of mineral acids such as hydrochloric acid, nitric acid, sulphuric acid or organic acids in particular acetic acid, or oxalic acid.

Further, any combination of the above dealumination methods is also possible.

The zeolite constitutes the catalytic phase. It can be used alone or mixed with a mineral matrix. In the description, the term "catalyst" means a catalyst formed entirely from zeolite or a mixture with a matrix prepared using techniques which are known to the skilled person.

To this end, the matrix can be selected from metal oxides such as aluminium, silicon and/or zirconium oxides, or from clays, more particularly kaolin, talc or montmorillonite.

The amount of active phase in the catalyst represents 5% to 100% of the weight of the catalyst.

The catalysts can be in different forms in the process of the invention: powder, formed products such as granules (for example, extrudates or beads), pellets, which are obtained by extrusion, moulding, compacting or any other known type of process. In practice, on an industrial scale, these are in the form of granules or beads which have the greatest advantages both on the basis of efficiency and on the basis of ease of use.

The zeolite used is preferably in its acid form. If necessary, a treatment is carried out which renders it acidic.

To this end, conventional treatments are used.

Thus the alkaline cations can be exchanged by treating the zeolite with ammonium thus leading to exchange of the alkaline cation with an ammonium ion, then calcining the exchanged zeolite to thermally decompose the ammonium cation and replace it with an H$^+$ ion.

The quantity of ammonia used is at least equal to the quantity necessary to exchange all of the alkaline cations for NH$_4^+$ ions.

Thus 10$^{-5}$ to 5×10$^{-3}$ moles of ammonia per gram of zeolite is used.

The exchangeable cation is exchanged with NH$_4^+$ at a temperature which is between ambient temperature and the reflux temperature of the reaction medium. The operation takes several hours and can be repeated.

The zeolite can also be acidified by carrying out a conventional acid treatment. This treatment can be carried out by adding an acid such as hydrochloric acid, sulphuric acid, nitric acid, perchloric acid, phosphoric acid or trifluoromethanesulphonic acid.

In a preferred implementation, the zeolite is acidified by passing a volume of acid, with a normality in the range 0.1 to 2 N per gram of zeolite, in the range 10 ml/g to 100 ml/g. This passage can be carried out in a single step or preferably in several successive steps.

The reaction of the benzyl alcohol with formula (I) with the alkanol with formula (II) can be carried out in the presence or in the absence of an organic solvent; one of the reactants can be used as the reaction solvent.

Non-limiting examples of solvents which are suitable for the present invention which can be cited are: aliphatic, cycloaliphatic or aromatic ether-oxides, more particularly diethyl oxide, dipropyl oxide, diisopropyl oxide, dibutyl oxide, methyltertiobutyl ether, dipentyl oxide, diisopentyl oxide, phenyl oxide, or benzyl oxide; dioxane, or tetrahydrofuran (THF).

When the process is carried out batchwise, the catalyst can represent, by weight with respect to the reactant, 2% to 50%, preferably 5% to 20%. However, if the process is carried out continuously, for example by reacting a mixture of benzyl alcohol and an alkanol on a fixed catalyst bed, these catalyst/benzyl alcohol ratios make no sense and at a given moment, there can be an excess weight of catalyst with respect to the starting benzyl alcohol.

The quantity of alkanol with formula (II), expressed in moles of alkanol per mole of benzyl alcohol with formula (I), can also vary between wide limits. The mole ratio of alkanol with formula (II)/benzyl alcohol with formula (I) can be between 1 and 30. The upper limit is not critical but however, for reasons of economy, there is no point in exceeding it.

The reaction temperature of the etherification reaction can vary b wide limits. It is advantageously between 50° C. and 200° C., more particularly between 50° C. and 100° C.

In general, the reaction is carried out at atmospheric pressure but higher pressures of 1 to 50 bars may also be suitable, preferably 1 to 25 bars. When the reaction temperature is higher than the boiling point of the reactants and/or products, autogenous pressure conditions are used.

The reaction is preferably carried out under a controlled atmosphere of inert gases such as nitrogen or the rare gases, for example argon.

The reaction time is also highly variable. It is normally between 15 minutes and 10 hours, preferably between 30 minutes and 5 hours.

From a practical viewpoint, the process can be carried out batchwise or continuously.

In a first variation, the catalyst, alkanol with formula (II) and optional organic solvent can be charged then the benzyl alcohol is introduced. In a preferred mode of the invention, the benzyl alcohol is introduced slowly, continuously or in fractions then the reaction mixture is heated to the desired temperature.

In a further variation of the invention, the reaction is carried out continuously, in a tube reactor comprising the solid catalyst disposed in a fixed bed.

The benzyl alcohol and the alkanol are preferably introduced separately.

They can also be introduced into a solvent, as mentioned above.

The residence time for the material flow on the catalytic bed is, for example, in the range 15 minutes to 10 hours, preferably in the range 30 minutes to 5 hours.

At the end of the reaction, a liquid phase comprising the etherified benzyl alcohol is recovered in a conventional manner.

The process of the invention produces etherified benzyl type alcohols, preferably with formula (III):

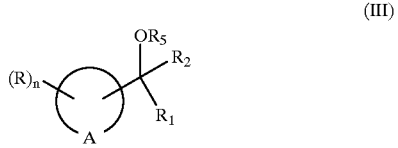
(III)

where:

A, n, $R_1$, $R_2$ and $R_5$ have the meanings given above.

More particularly, preferred compounds of the invention have formula (IIIa):

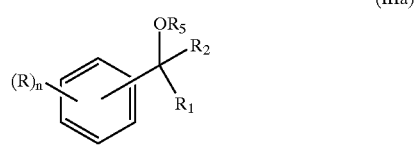
(IIIa)

where:

n, R, $R_1$, $R_2$ and $R_5$ have the meanings given above.

The process of the invention is particularly suitable for the preparation of ($C_1$–$C_4$)alkyl ethers, and cycloalkyl vanillic alcohol.

The present invention also provides perfuming compositions, products and perfuming substances, characterized in that they comprise, as an active principal with an influence on odour, an effective quantity of at least one etherified benzyl type alcohol (III) or (IIIa).

The different ethers obtained have interesting olfactive properties and can, inter alia, be used to prepare perfuming compositions and perfumed products.

Methyl 4-hydroxy-3-methoxybenzyl ether and cyclohexyl 4-hydroxy-3-methoxybenzyl ether are distinguished by their respective odour of praline for the first and leather for the latter.

The term "perfuming compositions" means mixtures of a variety of ingredients such as solvents, solid or liquid supports, fixatives, various odorous compounds, etc . . . , into which the etherified benzyl type alcohol (III) or (IIIa) has been incorporated, which mixtures are used to produce the desired fragrance in a variety of types of finished products.

Perfume bases constitute preferred examples of fragrancing compositions in which the etherified benzyl type alcohol (III) or (IIIa) can advantageously be used.

Eaux de toilettes, after-shave lotions, perfumes, soaps, bath or shower gels or deodorant or antiperspirant products in the form of sticks or lotions are examples of finished products or substances to which the etherified benzyl type alcohol (III) or (IIIa) provides its original note.

They can also be used in shampoos and in all types of hair care product.

They can also perfume any type of talc or powder.

They may also be suitable for air fresheners or any cleaning product.

A further example of compositions into which said compounds can advantageously be introduced is represented by the usual detergent products. These compositions generally comprise one or more of the following ingredients: anionic, cationic or amphoteric surfactants, bleaching agents, optical brighteners, various fillers, anti-redeposition agents. The nature of these various components is not critical and the etherified benzyl type alcohol (III) or (IIIa) can be added to any type of detergent composition. They can be introduced into fabric softeners, in the liquid form or into compositions deposited on a support, usually a non-woven support, for use in clothes dryers.

In the compositions of the invention, the quantity of etherified benzyl type alcohol (III) or (IIIa), expressed as the percentage by in the composition under consideration, depends on the nature of said composition (perfume base or eau de toilette, for example), and on the power and nature of the desired effect in the final product. Clearly, in a perfume base the amount of etherified benzyl type alcohol (III) or (IIIa) can vary between wide limits, for example more than 5% by weight and can reach 90% by weight, while in a perfume, an eau de toilette or an after-shave lotion, this quantity can be much lower than 50% by weight.

The quantity of etherified benzyl type alcohol in detergent compositions, in particular in household detergents or in soaps, can be of the order of 0.01% to 2%.

They can also be present in perfumed shampoos in an amount of 0.005% to 2%, or can perfume any hair care product.

The lower limit of the etherified benzyl type alcohol (III) or (IIIa) content can be that which causes a perceptible modification of the scent of the fragrance or the note of the finished product. In some cases, this minimum content can be of the order of 0.001% by weight. Clearly, amounts which are not included within the limits indicated above can be used without in any way departing from the scope of the present invention.

Examples of embodiments of the invention will now be given.

The following examples illustrate the invention without in any way limiting its scope.

The terms "conversion" and "selectivity" mean:

$$\text{Degree of conversion } (TT) = \frac{\text{number of moles of benzyl alcohol transformed}}{\text{number of moles of benzyl alcohol introduced}} (\%)$$

$$\text{Yield } (RR) = \frac{\text{number of moles of hydroxyalkylated ether formed}}{\text{number of moles of benzyl alcohol introduced}} (\%)$$

EXAMPLES 1 TO 5

1. 5 g of vanillic alcohol (4-hydroxy-3-methoxybenzyl alcohol) and 25 g of aliphatic alcohol ROH were introduced into a 100 ml three-necked flask.

A catalyst comprising 40% of binder (alumina) and 60% of a β zeolite sold by PQ was used. The zeolite used was a zeolite with an Si/Al ratio of 12.5.

2 g of said zeolite, calcined at 500° C., was added.

It was stirred and heated to 80° C.

These conditions were maintained for 2 hours.

The catalyst was filtered.

The products obtained were analysed by gas phase chromatography.

The products were separated by distillation.

The product obtained using the following reaction is defined n Table (I):

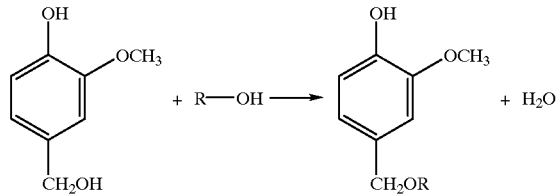

TABLE (I)

| Examples | R | TT % | RR % |
|---|---|---|---|
| 1 | $CH_3$ | 99 | 95 |
| 2 | $CH_3CH_2$ | 99 | 97 |
| 3 | $CH_3CH_2CH_2$ | 99 | 97 |
| 4 | $CH(CH_3)_2$ | 99 | 95 |
| 5 | $C(CH_3)_3$ | 55 | 37 |

2. The product of Example 2, namely methyl 4-hydroxy-3-methoxybenzyl ether, had an odour of praline while those of Examples 3 and 4 had a slight vanilla odour.

EXAMPLE 6

1. Example 1 was repeated with the exception that cyclohexanol was used.

The following results were obtained:

TT=99%

RR=96%

2. The cyclohexyl 4-hydroxy-3-methoxybenzyl ether represented by the following formula had a leather odour.

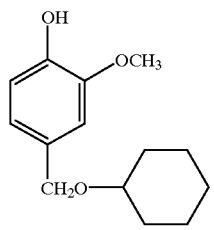

EXAMPLES 7 TO 9

1. The method of Example 1 was repeated.

$$Ar\text{—}CH_2OH + CH_3OH \rightarrow Ar\text{—}CH_2\text{—}O\text{—}CH_3 + H_2O$$

The results obtained are shown in Table (II).

TABLE (II)

| Examples | Ar | TT | RR |
|---|---|---|---|
| 7 | 20/1 | 99 | 85 |
| 8 | 20/2 | 99 | 97 |
| 9 | 20/3 | 99 | 94 |

2. The products from Examples 8 and 9 had respectively an animal naphthalene and an aniseed-cheese odour.

EXAMPLES 10 AND 11

Example 1 was repeated using a secondary alcohol.

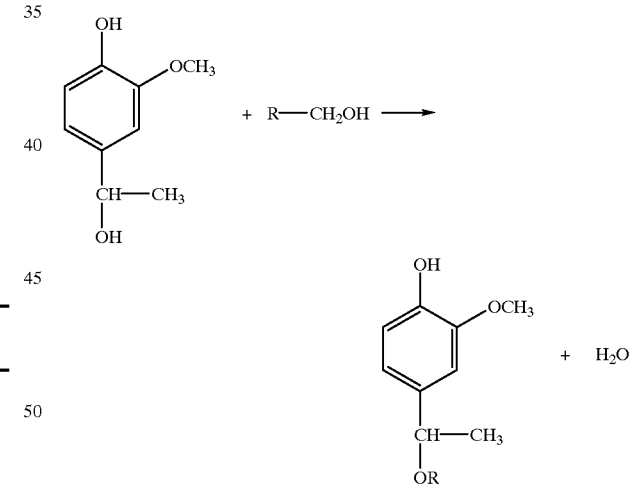

The results obtained are shown in Table (III).

TABLE (III)

| Examples | R | TT % | RR % |
|---|---|---|---|
| 10 | $CH_3$ | 99 | 95 |
| 11 | $CH_3CH_2$ | 99 | 96 |

EXAMPLES 12 AND 13

Example 1 was repeated using an unsaturated alcohol.

The results obtained are shown in Table (IV).

TABLE (IV)

| Examples | R | TT % | RR % |
|---|---|---|---|
| 12 | 21/1 | 100 | 85 |
| 13 | 21/2 | 100 | 95 |

EXAMPLES 14 AND 15

Example 1 was reproduced using a secondary alcohol.

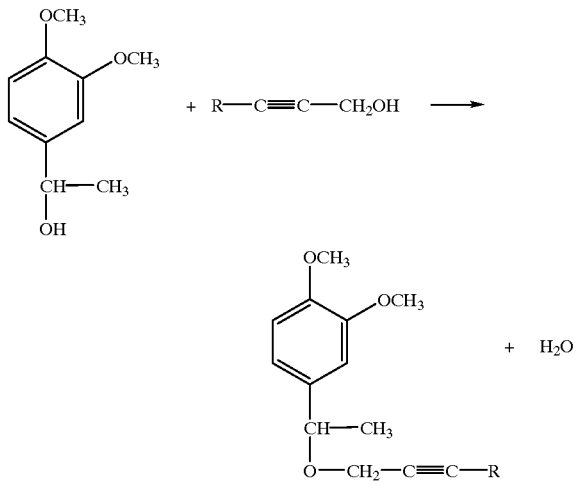

The results obtained are shown in Table (V).

TABLE (V)

| Examples | R | TT % | RR % |
|---|---|---|---|
| 14 | R=H | 100 | 85 |
| 15 | R=$CH_3$ | 100 | 90 |

What is claimed is:

1. A process for etherifying a benzyl alcohol compound, comprising the steps of: a) carrying out an etherification reaction of said alcohol compound with a reaction medium comprising an alkanol in the presence of a catalyst, and in the presence of an catalytically effective quantity of a zeolite in its acid form.

2. A process according to claim 1, wherein the benzyl alcohol compound has formula (I):

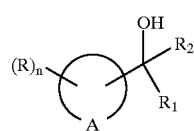

(1)

wherein:

A represents the residue of a cycle forming all or a portion of a carbocyclic or heterocyclic aromatic, monocyclic or polycyclic system comprising at least one group:

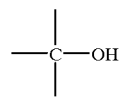

R represents one or more substituents which are identical or different;

$R_1$ and $R_2$, which are identical or different, represent a hydrogen atom, a functional group or a hydrocarbon group containing 1 to 24 carbon atoms, saturated or unsaturated, linear or branched acyclic aliphatic group; a saturated, unsaturated or aromatic, monocyclic or polycyclic cycloaliphatic group; or a saturated or unsaturated, linear or branched aliphatic group carrying a cyclic substituent;

$R_1$ and $R_2$ form a cycle, optionally comprising a further heteroatom; or one of groups $R_1$ and $R_2$ represents a group $CF_3$ n is a number equal to 5 or less.

3. A process according to claim 2, wherein $R_1$ and $R_2$ represent:

a saturated or unsaturated, linear or branched acyclic aliphatic group, optionally the hydrocarbon chain being interrupted by a heteroatom, a functional group or carrying substituents;

a saturated or unsaturated, linear or branched acyclic aliphatic group carrying a cyclic substituent, optionally substituted, said acyclic group optionally being connected to the cycle by a valence bond, a heteroatom or a functional group;

a carbocyclic group which is saturated or contains 1 or 2 unsaturated bonds in the cycle, containing 3 to 8 carbon atoms, said cycle being optionally substituted;

an aromatic carbocyclic group, containing at least 4 carbon atoms, said cycle being optionally substituted; and one of groups $R_1$ and $R_2$ represents a group $CF_3$.

4. A process according to claim 2, wherein A is the residue of a cyclic compound containing at least 4 atoms in the cycle and representing at least one of the following cycles:

an aromatic, monocyclic or polycyclic carbocycle; or an aromatic, monocyclic or polycyclic heterocycle containing at least one of the heteroatoms O, N and S.

5. A process according to claim 2, wherein A is a benzene or naphthalene cycle.

6. A process according to claim 2, wherein A carries one or more electron-donating groups.

7. A process according to claim 6, wherein the electron-donating group is:

a linear or branched alkyl group containing 1 to 6 carbon atoms;

a linear or branched alkenyl group, containing 2 to 6 carbon atoms;

a linear or branched halogenoalkyl group containing 1 to 6 carbon atoms, cycloalkyl group containing 3 to 6 carbon atoms;

a phenyl group;

a hydroxyl group;

a $NO_2$ group;

an alkoxy $R_3$—O— or thioether $R_3$—S—, wherein $R_3$ represents a linear or branched alkyl group containing 1 to 6 carbon atoms, or a phenyl group;

a —N—(R$_4$)$_2$ group wherein R$_4$, which is identical or different, represents a hydrogen atom, a linear or branched alkyl group containing 1 to 6 carbon atoms, or a phenyl group;

a —NH—CO—R$_4$ group, wherein group R$_4$ has the meaning given above;

a carboxy group or R$_4$—O—CO— radical wherein group R$_4$ has the meaning given above;

an acyloxy or aroyloxy R$_3$—CO—O— wherein group R$_3$ has the meaning given above;

a halogen atom; or a CF$_3$ group.

8. A process according to claim 2, wherein the benzyl alcohol compound has formula (Ia):

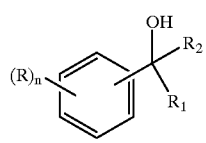

(Ia)

wherein:

n is a number equal to 4 or less;

group R is an electron-donating group;

groups R$_1$ and R$_2$, which are identical or different, represent:

a hydrogen atom;

a linear or branched alkyl group containing 1 to 6 carbon atoms;

a cycloalkyl group containing 3 to 8 carbon atoms;

a phenyl group;

a phenylalkyl group containing 7 to 12 carbon atoms; or a CF$_3$ group.

9. A process according to claim 1, wherein the benzyl alcohol compound is:

vanillic alcohol;

p-hydroxybenzyl alcohol;

1-(4-hydroxy-3-methoxyphenyl)ethanol;

2-hydroxybenzyl alcohol;

p-methoxybenzyl alcohol;

3,4-dimethoxybenzyl alcohol;

6-n-propyl-3,4-dimethoxybenzyl alcohol;

(3,4-dimethoxyphenyl)dimethylcarbinol;

1-[1-hydroxy-2-methylpropyl]-3,4-dimethoxybenzene;

1-[1-hydroxy-2-methylpropyl]-3,4-diethoxybenzene;

1-[1-hydroxyethyl]-3,4-diethoxybenzene;

1-[1-hydroxyethyl]-3,4-dimethoxy-6-propylbenzene;

5-[1-hydroxyethyl]-1,3-benzodioxol; or naphthalene-2-methylol.

10. A process according to claim 1, wherein the alkanol has general formula (II):

R$_5$—OH (II)

wherein:

R$_5$ represents a hydrocarbon group containing 1 to 24 carbon atoms, which is a saturated or unsaturated, linear or branched acyclic aliphatic group; a saturated, unsaturated or aromatic cycloaliphatic group; or a saturated or unsaturated, linear or branched aliphatic group carrying a cyclic substituent.

11. A process according to claim 10, wherein R$_5$ represents:

a saturated or unsaturated, linear or branched acyclic aliphatic group, optionally the hydrocarbon chain being interrupted by a functional group or carries substituents;

a saturated or unsaturated linear or branched acyclic aliphatic group carrying a cyclic substituent, optionally substituted, said acyclic group being connected by a valence bond, a heteroatom or a functional group; or a carbocyclic group which is saturated or comprises 1 or 2 unsaturated bonds in the cycle, containing 3 to 7 carbon atoms, said cycle being substituted.

12. A process according to claim 11, wherein R$_5$ represents a linear or branched alkyl, alkenyl, alkadienyl or alkynyl group, containing 1 to 24 carbon atoms.

13. A process according to claim 11, wherein the alkanol is a terpene alcohol with formula (IIa):

T—OH (IIa)

wherein T represents a terpene alcohol residue containing multiples of 5 carbon atoms.

14. A process according to claim 13, wherein T represents a hydrocarbon group containing 5 to 40 carbon atoms, or a saturated, unsaturated or aromatic, monocyclic or polycyclic cycloaliphatic group, comprising cycles containing 3 to 8 carbon atoms.

15. A process according to claim 14, wherein T represents a saturated or unsaturated, linear or branched aliphatic group.

16. A process according to claim 13, wherein T represents the residue of:

a saturated or unsaturated, linear or branched aliphatic terpene alcohol;

a saturated or unsaturated monocyclic, cycloaliphatic or aromatic terpene alcohol; or a cycloaliphatic or polycyclic terpene alcohol containing at least two saturated or unsaturated carbocycles.

17. A process according to claim 1, wherein the alkanol is:

methanol;

ethanol;

trifluoroethanol;

propanol, isopropyl alcohol;

butanol, isobutyl alcohol, sec-butyl alcohol, tert-butyl alcohol;

pentanol, isopentyl alcohol, sec-pentyl alcohol and tert-pentyl alcohol;

3-chlorobut-2-en-1-ol;

2-butyn-1-ol;

3,7-dimethyloct-6-en-1-ol;

chrysanthemic alcohol;

3,7-dimethyloctanol;

geraniol;

linalool;

citronellol;

hydroxycitronellol;

nerol, thymol;

menthol;

isoborneol; or verbenol.

18. A process according to claim 1, wherein the catalyst is a natural or synthetic zeolite.

19. A process according to claim 18, wherein the zeolite is an acidic zeolite.

20. A process according to claim 18, wherein the zeolite is a natural zeolite, a synthetic zeolite with a unidimensional network, a zeolite with a two-dimensional network, a zeolite with a three dimensional network, a mesoporous MCM zeolite.

21. A process according to claim 20, wherein the zeolite is:

chabazite, cliniptilolite, erionite, phillipsite and offretite, ZSM-4 zeolite, L zeolite, ZSM-12 zeolite, ZSM-22 zeolite, ZSM-23 zeolite, ZSM-48 zeolite, mordenite, ferrierite, β zeolite, Y zeolite, X zeolite, ZSM-5 zeolite, ZSM-11 zeolite, or offretite.

22. A process according to claim 21, wherein the zeolite is a β zeolite.

23. A process according to claim 22, wherein the zeolite is used alone or mixed with a mineral matrix.

24. A process according to claim 23, wherein the mineral matrix is aluminum oxide, silicon oxide, zirconium oxide, clays, kaolin, talc or montmorillonite.

25. A process according to claim 1, wherein the ratio between the number of moles of alkanol and the number of moles of benzyl alcohol compound is in the range 1 to 30.

26. A process according to claim 1, wherein the quantity of catalyst represents, by weight with respect to the reactant, 2% to 50%.

27. A process according to claim 26, wherein the quantity is 5% to 20%.

28. A process according to claim 1, wherein the etherification reaction is carried out at a temperature in the range 50° C. to 200° C.

29. A process according to claim 28, wherein the temperature is in the range 50° C. to 100° C.

30. A process according to claim 1, wherein the etherification reaction is carried out at atmospheric pressure.

31. A process according to claim 1, wherein the catalyst is in the form of a catalytic bed and residence time for the reaction medium is in the range 15 minutes to 10 hours.

32. A process according to claim 1, further comprising the step of:

b) recovering a liquid phase comprising the etherified benzyl alcohol compound from which said etherified benzyl alcohol compound is recovered.

33. A perfuming ingredient which is cyclohexyl 4-hydroxy-3-methoxybenzyl.

34. A perfumed composition, comprising cyclohexyl 4-hydroxy-3-methoxybenzyl ether.

35. A process for the preparation of a perfumed composition, comprising the step of adding an effective perfuming quantity of cyclohexyl 4-hydroxy-3-methoxybenzyl ether, to said composition.

36. A perfumed composition made by the process of claim 35, which is in the form of a perfume, eau de toilette, after-shave lotion, perfume, soap, bath gel, shower gel, deodorant, antiperspirant, shampoo, hair care product, powder, talc, air freshener, cleaning product, detergent, or fabric conditioner.

37. Cyclohexyl 4-hydroxy-3-methoxybenzyl ether.

* * * * *